(12) United States Patent
Zaiser et al.

(10) Patent No.: US 8,307,828 B2
(45) Date of Patent: Nov. 13, 2012

(54) PNEUMATIC SINGLE-LUMEN MEDICAL GAS CONSERVER

(75) Inventors: LeNoir E. Zaiser, Naples, FL (US); Kevin W. Confoy, Naples, FL (US)

(73) Assignee: Inovo, Inc., Naples, FL (US)

( * ) Notice: Subject to any disclaimer, the term of this patent is extended or adjusted under 35 U.S.C. 154(b) by 1327 days.

(21) Appl. No.: 11/844,907

(22) Filed: Aug. 24, 2007

(65) Prior Publication Data

US 2008/0173304 A1 Jul. 24, 2008

Related U.S. Application Data

(60) Provisional application No. 60/823,456, filed on Aug. 24, 2006.

(51) Int. Cl.
*A61M 16/20* (2006.01)
*A62B 9/02* (2006.01)

(52) U.S. Cl. ......... 128/205.24; 128/201.28; 128/204.18; 128/204.26; 128/207.12; 128/207.16

(58) Field of Classification Search ............ 128/205.24, 128/201.28, 203.12, 204.18, 204.26, 207.12, 128/207.16, 200.21, 200.14, 200.19, 202.27, 128/203.19, 203.21, 207.14, 203.27; 239/338, 239/370

See application file for complete search history.

(56) References Cited

U.S. PATENT DOCUMENTS

| | | | | |
|---|---|---|---|---|
| 5,881,725 | A * | 3/1999 | Hoffman et al. | 128/204.26 |
| 6,484,721 | B1 * | 11/2002 | Bliss | 128/205.24 |
| 2003/0075179 | A1 * | 4/2003 | Gale et al. | 128/204.26 |
| 2004/0154693 | A1 * | 8/2004 | Zaiser et al. | 141/83 |
| 2006/0219245 | A1 * | 10/2006 | Holder | 128/204.26 |

FOREIGN PATENT DOCUMENTS

WO WO 2006092635 A1 * 9/2006

* cited by examiner

*Primary Examiner* — Clinton T. Ostrup

(57) ABSTRACT

A pneumatic single-lumen medical gas conserver combines the advantages of typical single-lumen and dual-lumen conservers. In particular, a pneumatic single-lumen conserver can provide a rapid response to patient inhalations without the need for a more expensive dual-lumen cannula hose. In addition, after delivering oxygen the conserver has a specific pneumatically-implemented delay period before being able to detect the next inhalation to inhibit "double pulse" deliveries. In addition to a conserving or pulse flow mode, the conserver can provide a user-selectable gas flow at a continuous or constant flow mode.

17 Claims, 8 Drawing Sheets

PNEUMATIC SINGLE-LUMEN MEDICAL GAS CONSERVER

RELATED APPLICATION(S)

This application claims the benefit of U.S. Provisional Application No. 60/823,456, filed on Aug. 24, 2006. The entire teachings of the above application are incorporated herein by reference.

BACKGROUND

Gas-conserving regulators include oxygen regulators, which are used to supply a patient with a regulated flow of oxygen. The oxygen is supplied by a source of highly-compressed oxygen, such as from a supply tank, which has its pressure reduced to a low pressure (e.g., 22 PSI) for delivery to the patient. Typical oxygen regulators employ a back-pressure piston to supply a continuous flow of that low pressure oxygen to the patient. Much of that oxygen is wasted because it is not inhaled by the patient.

To reduce the amount of wasted oxygen, oxygen-conserving regulators have been developed. These conservers tend to limit the oxygen flow to periods of inhalation. The oxygen flow is typically controlled electronically or pneumatically. Of the pneumatic types, there are two common types of systems: single-lumen and dual-lumen.

In a typical electronic conserver, a solenoid valve controls the flow of oxygen to the patient. The solenoid valve can accurately open to provide the flow of oxygen to the patient when the patient inhales, and close between breaths. Typically, the solenoid valve has high energy requirements and is battery powered.

In typical dual lumen pneumatic conserving regulators, a reservoir coupled to the oxygen source holds a supply of oxygen for delivery to the patient. Delivery of the oxygen is controlled by a slave diaphragm that separates the reservoir from a control gas chamber. The slave diaphragm seals the opening to a delivery nozzle when the patient is not inhaling and releases the seal from the nozzle opening when the patient inhales. The slave diaphragm is made from a flexible material and is generally pressurized toward the closed position. Operation of the slave diaphragm is controlled by a pilot diaphragm, which is coupled to the patient. When the patient inhales, the pilot diaphragm lifts off an orifice pneumatically connected to the control gas chamber. The oxygen in the control gas chamber is then expelled, creating a pressure drop sufficient to allow the slave diaphragm to move away from the slave nozzle, thus allowing flow to the patient.

Dual-lumen devices use a cannula with two separate hoses for connecting to the conserver. Depending on the design of the cannula, each hose either serves one or both nostrils of the patient. The conserver likewise has two cannula hose ports. A sensing or pilot port is used exclusively for sensing the vacuum caused by patient inhalation. A slave or delivery port is used exclusively for delivery of oxygen to the patient.

When the patient inhales, oxygen is delivered by the delivery port through a delivery hose until inhalation ends. Because the two hoses of the cannula do not intermingle, the conserver is able to deliver oxygen the entire time the patient is inhaling. Therefore, dual-lumen conservers are commonly called "demand" conservers.

In a typical dual-lumen conserver (i.e., demand conserver), when the patient stops inhaling—causing the pilot diaphragm to close—the control chamber builds back to operating pressure (e.g., 22 PSI) almost immediately. Consequently, when the pilot diaphragm shuts against the pilot nozzle, flow to the patient stops. This is usually done by having a preset control flow between 100 cc and 350 cc per minute, depending on the design of the device. The need to stop flow as soon as the pilot diaphragm closes is because, in a demand conserver, the pilot diaphragm stays open as long as the patient inhales. The dual-lumen design of such conservers allows the unit to be sensitive enough to sense the vacuum caused by inhalation.

In comparison, a typical single-lumen conserver does not have that sensitivity. Single-lumen conservers use only a single cannula hose that serves both nostrils, which is coupled to a single port on the conserver. When no oxygen is flowing through the hose, the conserver can detect when the patient inhales, and oxygen delivery begins. However, once oxygen begins to flow through the hose, the flow of oxygen to the patient overwhelms the device's ability to sense the vacuum caused by the patient during inhalation and the device will no longer be able to sense when inhalation ends. Therefore, the device is constructed to stop the flow of oxygen after a predetermined amount of time, regardless of the patient's breathing pattern. There are some pneumatic devices that work this way, and all electronic devices work this way. These conservers are called "pulse" conservers, as they typically give a large pulse of oxygen and then shut themselves off and wait for the next breath.

Typically, dual-lumen conservers have the advantage of much better performance under all breathing conditions, meaning they deliver the correct amount of oxygen for the patient and work well with the widest variety of breathing patterns. Also, dual-lumen devices can have continuous or constant flow at all settings if required, whereas single-lumen devices typically have only a single continuous flow setting, such as a constant 2 liters per minute (LPM).

In comparison, single-lumen conservers have the advantages of a simpler (and less expensive) cannula hose, and because they only deliver a pulse of oxygen, these conservers can have a higher conservation ratio (many respiratory professionals believe that oxygen delivered at the end of inhalation is wasted because it does not get to the lungs before being exhaled). However, by controlling the rate of flow after the initial burst of oxygen, a dual-lumen device can be manufactured to conserve as much as a single lumen device.

One disadvantage of single-lumen pneumatic conservers is that they may be too quick to detect a breath after delivering oxygen. This problem is especially acute when the patient has a long breathing pattern (i.e. few breaths per minute). Because such a patient may still be inhaling on the same breath after oxygen is delivered, the patient may receive a "double pulse" or "multiple pulses" of oxygen for each breath. Electronic conservers generally avoid that problem by not registering a new inhalation until a specified period of time has elapsed since the last detection.

Furthermore, in typical prior art oxygen-conserving regulators, the inhaling patient receives an initial burst of oxygen from a bolus reservoir, often followed by a steady flow of oxygen at the regulator's flow rate while inhalation continues or until delivery is stopped. The initial burst volume of gas delivered to the patient at inspiration is equal to the volume of the reservoir multiplied by the pressure of the gas in the reservoir.

Some examples of oxygen-conserving regulators are described in U.S. Pat. Nos. 6,116,242 to Frye et al., 6,364,161 to Pryor, and 6,752,152 to Gale et al. Other embodiments are described in U.S. application Ser. No. 10/666,115 entitled "Differential Pressure Valve Employing Near-Balanced Pressure" by LeNoir E. Zaiser, which was filed on Sep. 19, 2003 (U.S. Publication No. 20040194829); U.S. application Ser. No. 10/706,872 entitled "Gas Conserving Regulator" by LeNoir E. Zaiser, et al., which was filed on Nov. 12, 2003 (U.S. Publication No. 20040154693); and U.S. application Ser. No. 10/772,220 entitled "Hybrid Electro-Pneumatic Conserver for Oxygen Conserving Regulator" by LeNoir E. Zaiser, et al., which was filed on Feb. 4, 2004 (U.S. Publication No. 20050039752). The teachings of those patents and applications are incorporated herein by reference in their entirety.

SUMMARY

In accordance with particular embodiments of the invention, a pneumatic single-lumen medical gas conserver combines the advantages of typical single- and dual-lumen conservers. In particular, a pneumatic single-lumen conserver can provide a rapid response to patient inhalations without the need for a more expensive dual-lumen cannula hose. In addition, after delivering oxygen the conserver has a specific pneumatically-implemented delay period before being able to detect the next inhalation to inhibit "double pulse" deliveries.

In accordance with a particular embodiment, a pneumatic medical gas conserver for providing a volume of medical gas to a patient can include a supply port, a patient port, a sensing valve, and a check valve. The supply port receives a regulated flow of a medical gas and the patient port provides a flow of medical gas to a patient through a single-lumen cannula.

The sensing valve is in gaseous communication with the patient port and can detect an inhalation by the patient so as to trigger delivery of the medical gas to the patient port.

The check valve can be gaseously disposed between the sensing valve and the patient port. The check valve can decouple the sensing valve from the patient port in response to detection of the inhalation by the sensing valve. More particularly, the check valve can decouple the sensing valve from the patient port before the medical gas is delivered to the patient port, in which case the decoupled sensing valve can be gaseously isolated from the delivered medical gas.

The conserver can further include a gas regulator in gas communication with the supply port.

In accordance with another particular embodiment, a pneumatic medical gas conserver for providing a volume of medical gas to a patient can include a patient port, a supply port, a delivery valve, a control valve, a sensing valve, and a check valve.

The patient port can be coupled to a single-lumen cannula and the supply port can receive a regulated flow of a medical gas;

The delivery valve can be gaseously disposed between the supply port and the patient port for controlling the flow of medical gas to the patient port. The conserver can further include a user-operable flow valve for selecting between a pulse delivery mode and a constant flow mode. In particular, the constant flow mode can cause the flow of medical gas to bypass the delivery valve.

The control valve can be in mechanical communication with the delivery valve and in gas communication with the supply port. The control valve can actuate the delivery valve. In addition, the control valve can be tuned to provide a fixed delivery cycle using, for example, an adjustable needle to vent gas and/or a timing orifice disposed in the gas flow path from the supply port to the control valve.

The sensing valve can be in gas communication with the control valve and the patient port. The sensing valve can detect an inhalation by the patient so as to trigger the control valve to begin a delivery cycle. In particular, the sensing valve can include a flexible membrane.

The check valve can be in mechanical communication with the control valve and gaseously disposed between the sensing valve and the patient port. The check valve can decouple the sensing valve from the patient port in response to the detection of the inhalation by the sensing valve.

The conserver can further include a gas regulator that can provide the regulated flow of medical gas from a pressurized supply of the medical gas. The gas regulator can be in gas communication with the supply port. The gas regulator can further provide a user selectable flow of medical gas from a plurality of flow settings.

In accordance with another particular embodiment, a pneumatic medical gas conserver for providing a volume of medical gas to a patient can include a housing, a gas flow regulator, a patient port, a user-operable mode selector, and a pneumatic delivery circuit.

The housing can be connectable to a supply of pressurized medical gas. The gas flow regulator can be within the housing and can provide a regulated flow of medical gas from the supply of pressurized medical gas. That regulated flow can include a user-selectable flow rate from a plurality of selectable flow rates.

The patient port can be within the housing and provides gas communication to a patient through a single-lumen cannula. The user-operable mode selector can be within the housing for providing the regulated flow of medical gas to the patient port at the selected flow rate in either a pulse flow mode or a constant flow mode.

The pneumatic delivery circuit can be within the housing and can receive the regulated flow of medical gas and deliver the received flow to the patient port in accordance with the mode selector. The delivery circuit can, in particular, include a delivery valve. The regulated flow of medical gas can bypasses the delivery valve when the mode selector is in the constant flow mode setting or the regulated flow of medical gas can travel through the delivery valve when the mode selector is in the constant flow mode setting.

BRIEF DESCRIPTION OF THE DRAWINGS

The foregoing and other objects, features, and advantages of the invention will be apparent from the following more particular description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Figure 1:
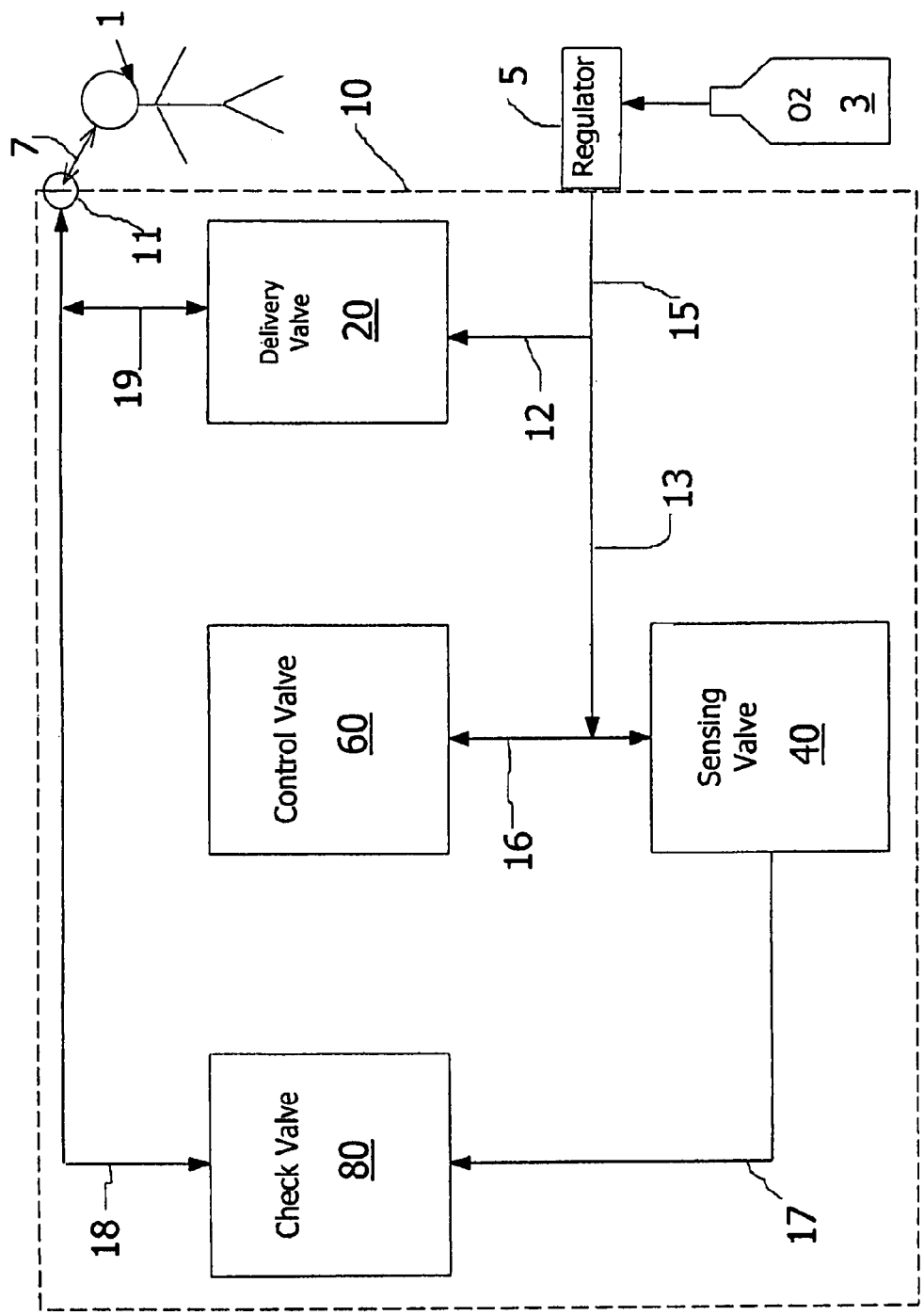
FIG. 1 is a schematic block diagram of a particular embodiment of a medical gas conserving device.

FIG. 1 is a schematic block diagram of a particular embodiment of a medical gas conserving device. A human or animal patient 1 receives a regulated volume of oxygen from a pressurized supply vessel 3 through a regulator 5 and conserver 10. Although not required, the regulator 5 and conserver 10 are typically part of a single physical unit that couples to the oxygen supply vessel 3. As shown, the patient 1 is in gas communication with the conserver 10 through a single-lumen cannula 7 coupled to a cannula port 11.

As shown, the conserver 10 includes four valves, a delivery valve 20, a sensing valve 40, a control valve 60, and a check valve 80. Gas passageways interconnect the valves and interface the conserver 10 with the regulator 5 and the cannula 7. A regulated flow of gas flows into a main supply passageway 15 from the regulator 5. The main supply passageway 15 supplies gas to two branch passageways, a delivery passageway 12 interconnected to the delivery valve 20 and a timing passageway 13, which in turn interconnects to a control passageway 16 coupling the control valve 60 with the sensing valve 40. The patient is coupled to the check valve 80 via a detection passageway 18 and to the delivery valve 20 via a flow passageway 19. The sensing valve and the check valve are interconnected by a sensing passageway 17.

Although the delivery passageway 12 and the timing passageway 13 are shown as being supplied by a common main supply passageway 15, that structure is not required. Instead, the timing passageway 13 can be tapped off from the delivery valve passageway 12 or separately supplied from the regulator 5. Additional valves and flow orifices may be present in physical embodiments, although not shown in the figures. Any suitable supply network can be employed and is contemplated by the following description.

Briefly, the conserver 10 delivers a volume of oxygen to the patient 1 in response to an inhalation. When the conserver detects an inhalation, using the sensing valve 40, oxygen begins flowing for a period of time controlled by the delivery valve 20. The specific volume is determined by the flow rate of the oxygen from the regulator 5 and the amount of time the delivery valve 20 is open. Once inhalation is detected, the check valve 80 decouples the sensing valve 40 from the patient 1 during the delivery cycle so that subsequent breathing actions do not affect the sensing valve 40—until the conserver 10 is ready to begin a new cycle.

Further details will be described below with respect to FIGS. 2-8. It should be understood that for clarity not all components are shown in the drawings, but the use and placement of such components is within the ability of those of ordinary skill in the art. Furthermore, it is understood that O-rings would commonly be used for sealing purposes, and that more or less O-rings, or different arrangements of O-rings, may be required in a physical product.

Figure 2:
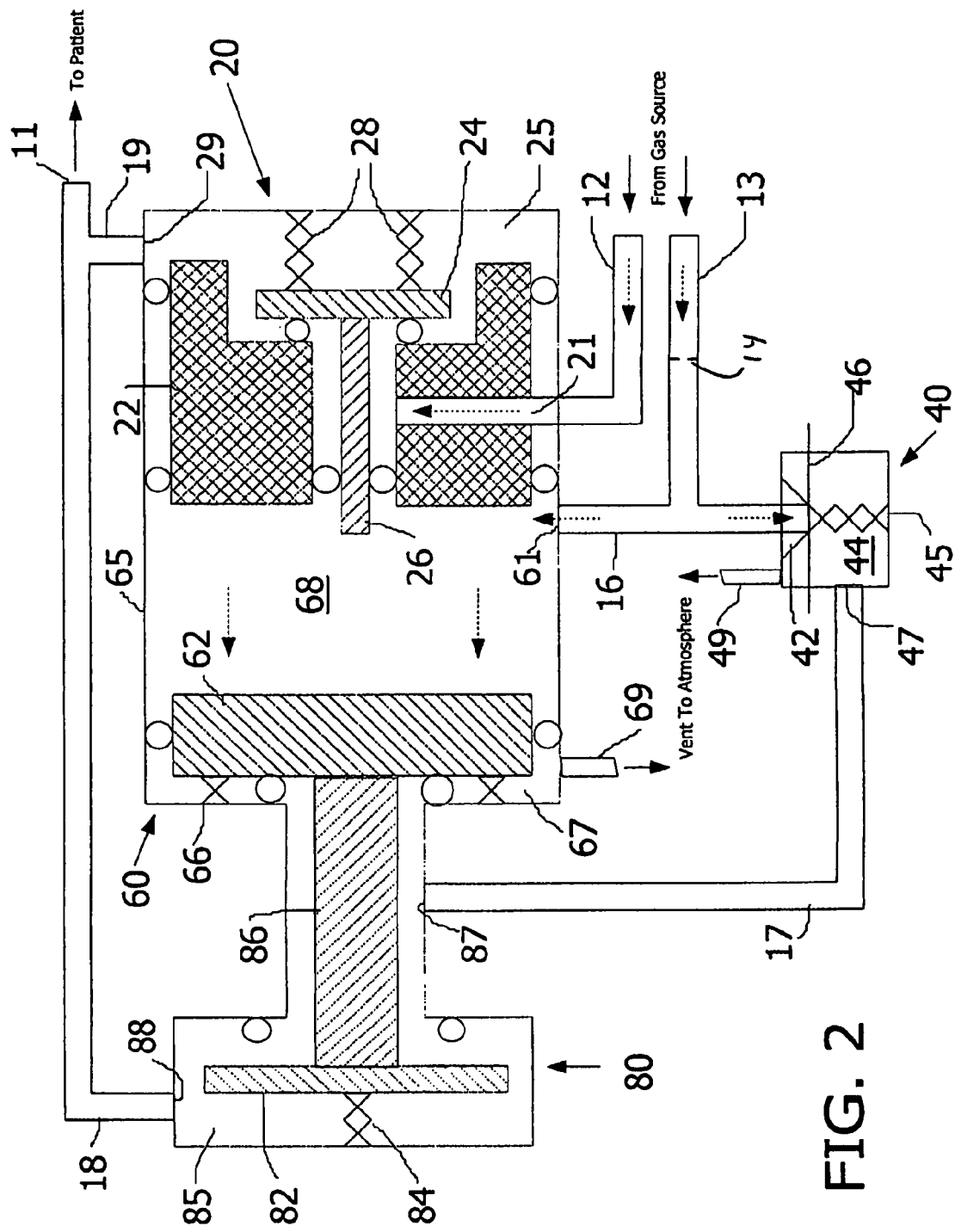
FIG. 2 is a schematic diagram of one embodiment of the conserving device of FIG. 1 at a steady-state condition.

FIG. 2 is a detailed schematic diagram of one embodiment of the conserving device 10 of FIG. 1 at a steady-state condition. In this state, the patient is not inhaling through the cannula and gas is not flowing to the cannula. The conserver 10 is ready and waiting to deliver oxygen.

The delivery valve 20 includes a delivery valve body 22, a delivery valve plate 24, a delivery actuating rod 26, and one or more delivery valve springs 28 operating in a delivery valve cavity 25. Oxygen enters the delivery valve 20 from the delivery passageway 12 through a delivery inlet 21 and exits to the flow passageway 19 through a delivery outlet 29. Note that unlike some prior pneumatic conservers, there is no gas reservoir to store oxygen for delivery to the patient.

The delivery valve 20 operates between the delivery inlet 21 and the delivery outlet 29 to open and close. As shown, the delivery valve 20 is closed, with the delivery valve plate 24 face sealed to the delivery valve body 22 through compression of the delivery valve plate 24 against an O-ring by the delivery valve springs 28. Because the delivery valve 20 is closed, no oxygen is being supplied to the patient. Note that the delivery actuating rod 26 is biased toward and extends into the control valve 60 by a known distance. The delivery valve plate 24 and actuating rod 26 are shown as being separate component parts, which can be fastened together, but the two features can be manufactured as a single valve element.

The control valve 60 includes a control piston 62 and one or more control springs 66. The control piston reciprocates within a piston cavity 65. An O-ring riding with the control piston 62 moveably divides the piston cavity into two chambers, a spring chamber 67 and a control gas chamber 68. The control gas chamber 68 is also bounded by the delivery valve body 22, which can be fixed within the piston cavity 65, with O-rings isolating the control chamber 68 from the delivery valve 20.

Oxygen from the timing passageway 13 is directed to a control passageway 16. As shown, the timing passageway includes a timing orifice 14 to reduce the timing gas flow rate. Oxygen supplied from the control passageway 16 enters the control chamber 68 through a control valve inlet 61 to pressurize the control chamber. In a particular embodiment the timing orifice has a diameter of 0.003 inches.

The spring chamber 67 is maintained at atmospheric pressure by a vent 69. As shown, the control chamber 68 is fully pressurized and the control piston 62 is face sealed against an O-ring.

The sensing valve 40 includes a nozzle 42 separated from a sensing chamber 44 by a flexible membrane 46, and a bias spring 45. The bias spring 46 biases the membrane 46 against the nozzle 42 to assist in closing the sensing valve 40. The nozzle is coupled to the control passageway 16, which in a particular embodiment interfaces with the sensing valve membrane 46 through a nozzle 42 opening having a diameter of 0.009 inches. Also shown is an atmospheric vent 49 and a sensing port 47 coupled to the sensing passageway 17. Further details of the sensing valve 40 are described in the above-incorporated U.S. application Ser. No. 10/666,115. As shown, the membrane 46 is sealing the nozzle 42 (and closing the sensing valve 40) so that oxygen cannot flow through the nozzle.

The check valve 80 includes a check plate 82, at least one spring 84, and an actuating rod 86. The check valve interfaces with the sensing passageway 17 through a sensing inlet 87 and with the detection passageway 18 through an outlet 88. The check valve spring 84 is biased to face seal the check plate 82 against an O-ring so as to disconnect the sensing inlet 87 from the outlet 88. As shown, the check valve 80 open, with the check plate 82 being unsealed. This occurs because the fully compressed control piston 62 has moved the actuating rod 86 to push the check valve plate 82 away from the sealing O-rings. The delivery valve plate 24 and actuating rod 26 are shown as being separate component parts, which can be fastened together, but the two features can be manufactured as a single valve element.

In the steady-state condition of FIG. 2, the conserver 10 is ready to supply oxygen to the patient. All that is needed to trigger a response is an inhalation from the patient, which would cause a vacuum in the detection passageway 18.

Figure 3:
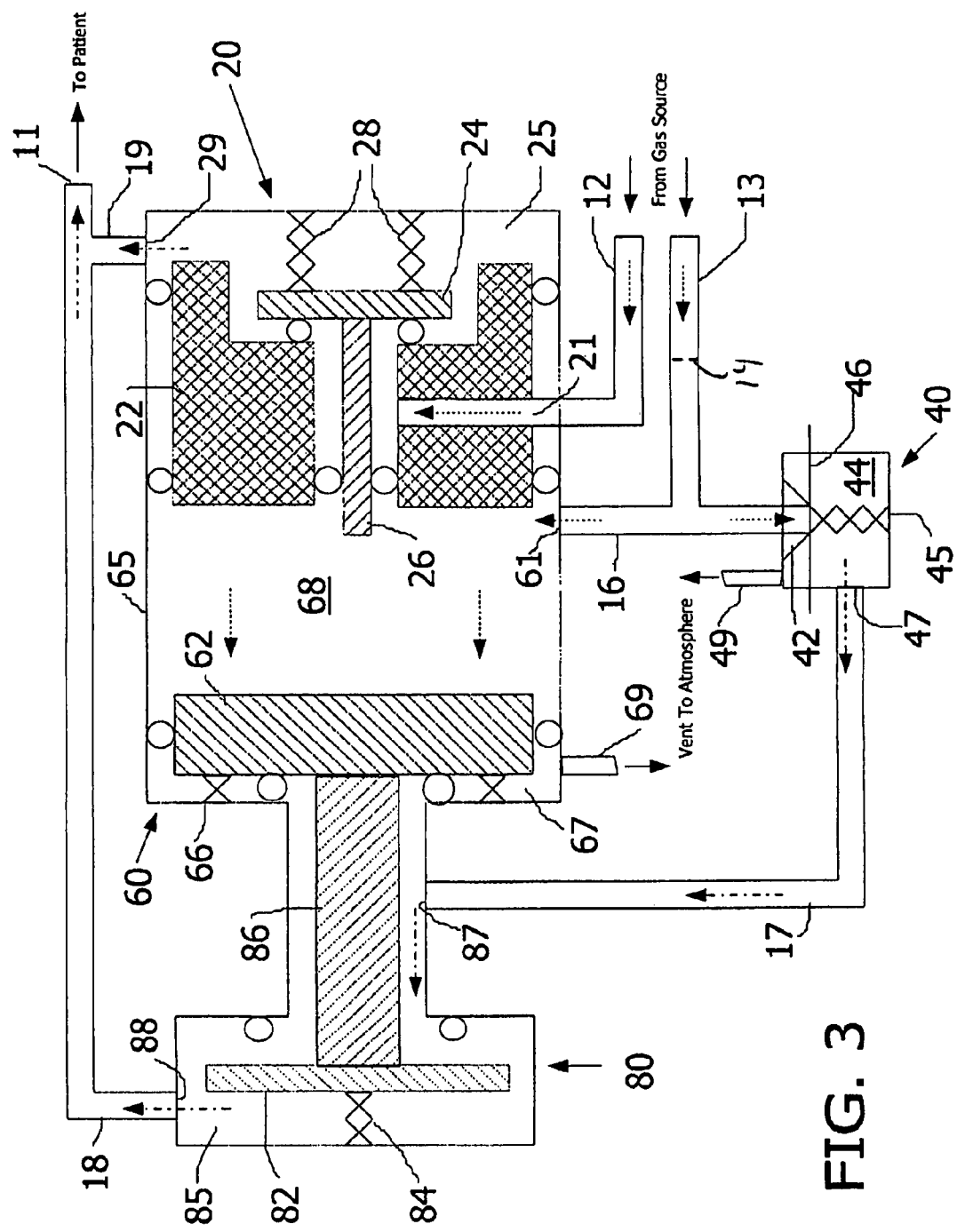
FIG. 3 is a schematic diagram of the conserving device of FIG. 2 illustrating gas flow in response to an inhalation by the patient 1.

FIG. 3 is a schematic diagram illustrating gas flow in response to an inhalation by the patient 1. As shown, inhalation draws atmospheric gas from the check valve 80, the sensing passageway 17, and the sensing chamber 44 through the detection passageway 18. That action results in a slight vacuum forming in the sensing chamber 44. The inhalation also tends to draw gas from the delivery valve 20.

Figure 4:
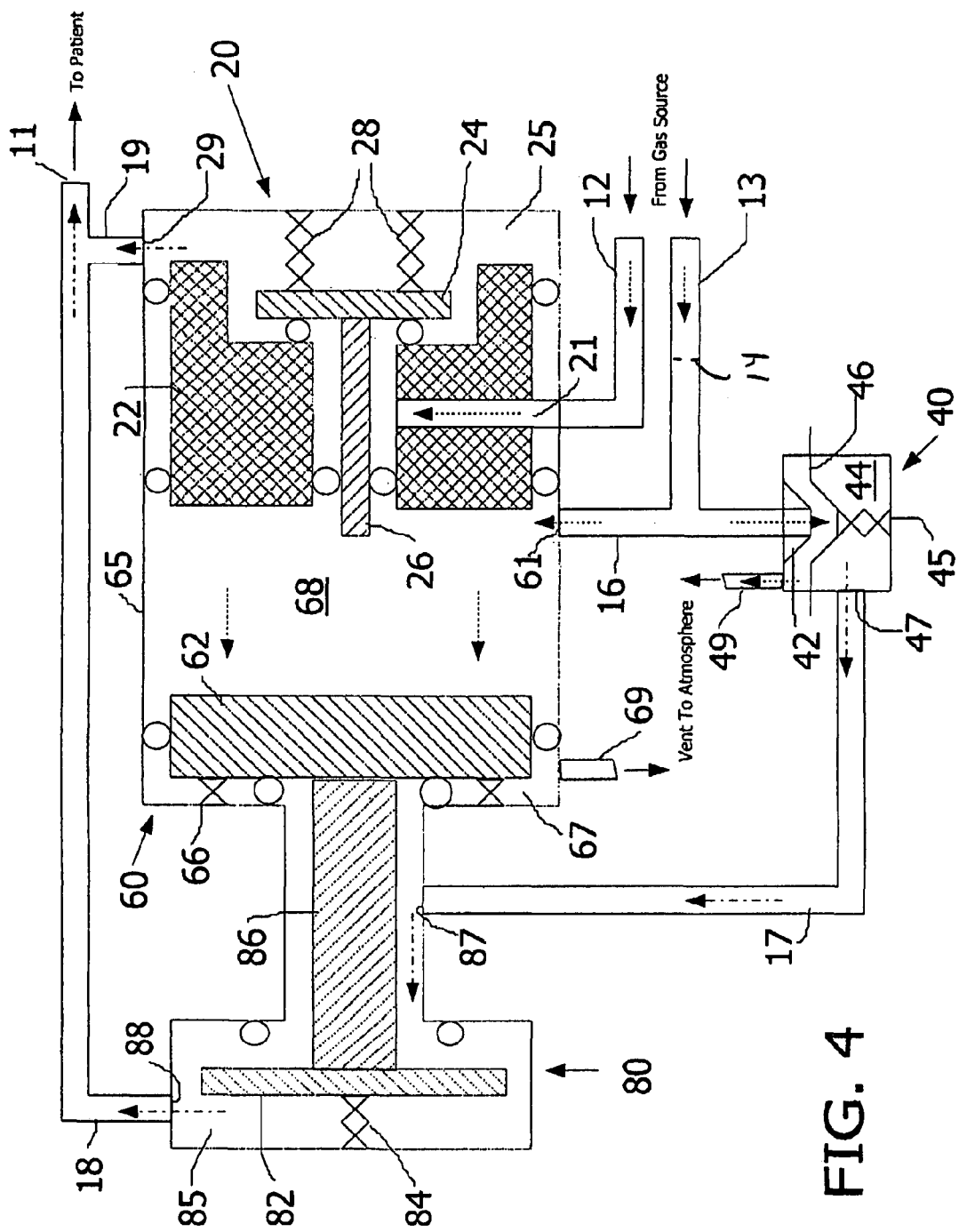
FIG. 4 is a schematic diagram of the conserving device of FIG. 2 illustrating the conserver's response to the inhalation of FIG. 3.

FIG. 4 is a schematic diagram illustrating the conserver's response to the inhalation of FIG. 3. The vacuum created in the sensing chamber 44 overcomes the force of the bias spring 45, which causes the membrane 46 to release from the nozzle 42. This immediately causes the low-pressure gas to flow from the control cavity 68 to atmosphere through the control passageway 16, the nozzle 42, and the vent 49. Note that in the delivery valve 20 the vacuum force is resisted by the delivery springs 28 to maintain the face seal on the delivery plate 24.

Figure 5:
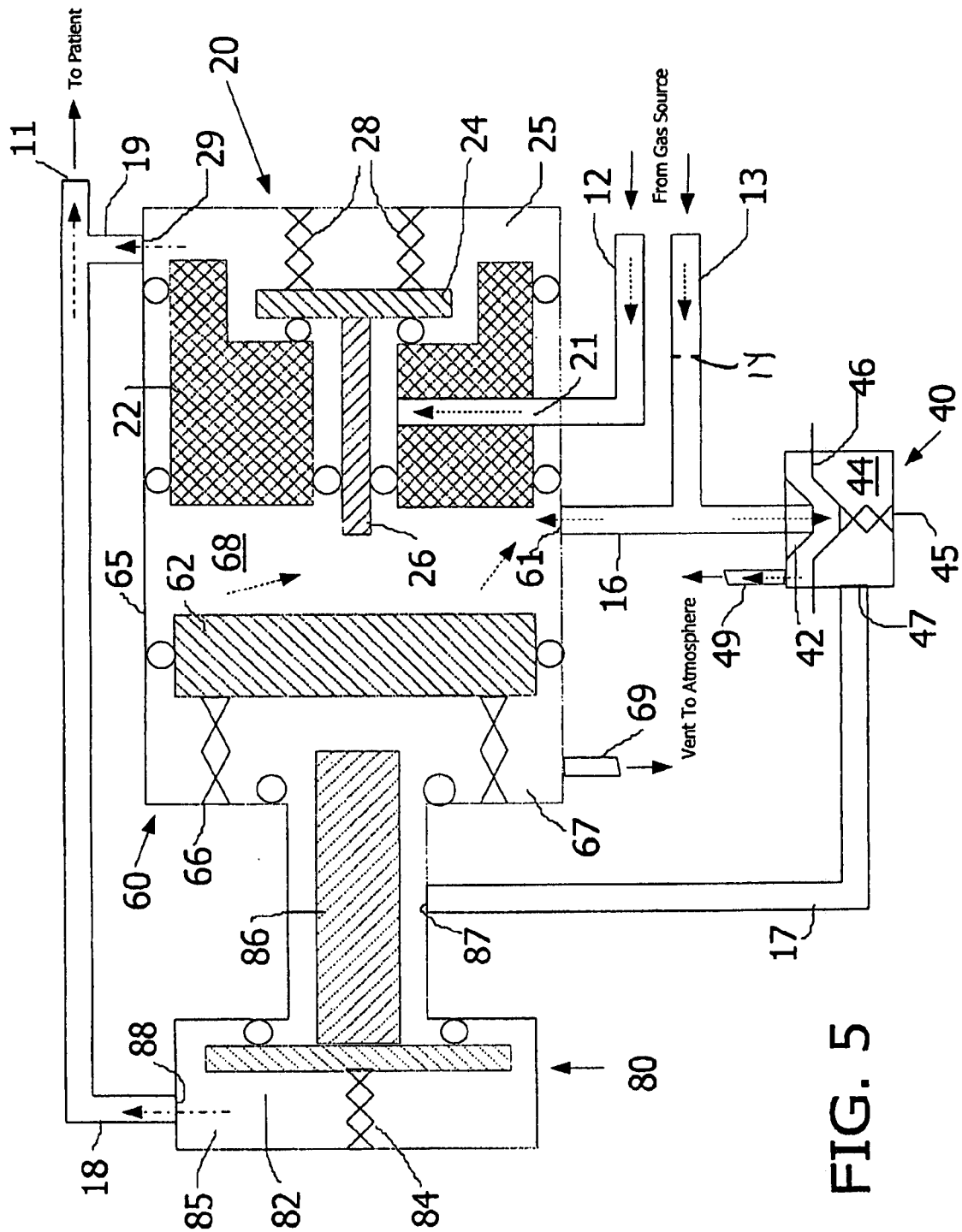
FIG. 5 is a schematic diagram of the conserving device of FIG. 2 illustrating the release of control gas.

FIG. 5 is a schematic diagram illustrating the release of control gas. As shown the low-pressure gas from the control gas chamber 68 continues to flow to atmosphere through the vent 49. As the control gas chamber 68 is evacuated, the control springs 66 urge the control piston 62 to lift off from the face seal and begin an upstroke. Once the face seal is released, the sensing chamber becomes coupled to the control spring chamber 67, which is maintained at atmospheric pressure by the control vent 69.

The movement of the control piston 62 also releases the check valve actuating rod 86, which allows the check valve spring 84 to compress the check valve plate 82 against its O-ring. The sensing chamber 44 is now decoupled from the patient, even though no oxygen is yet being delivered to the patient (i.e., the delivery valve 20 is closed). That decoupling protects the pilot diaphragm 46 from pressure shocks. Note that the check valve actuating rod 86 is biased toward and extends into the control spring chamber 67.

The upstroke of the control piston 62 aids in evacuating the control gas chamber 68 by maintaining pressure in the control gas chamber 68 above atmospheric pressure. The additional pressure caused by the control springs 66 helps to keep the sensing valve 40 open because the gas pressure in the nozzle 42 can continue to overcome the membrane 42 bias.

During the upstroke, the upward motion of the control piston 62 tends to create a vacuum in the control spring chamber 67 behind the piston. Because the sensing chamber 44 is coupled to the control spring chamber 67, such a vacuum would tend to hold the sensing valve 40 open. The control vent 69 to atmosphere tends to modulate this vacuum in the control spring chamber 67 and the sensing chamber 44 to avoid damage to the diaphragm 46. Note that no back-pressure is applied to the sensing chamber 44.

Figure 6:
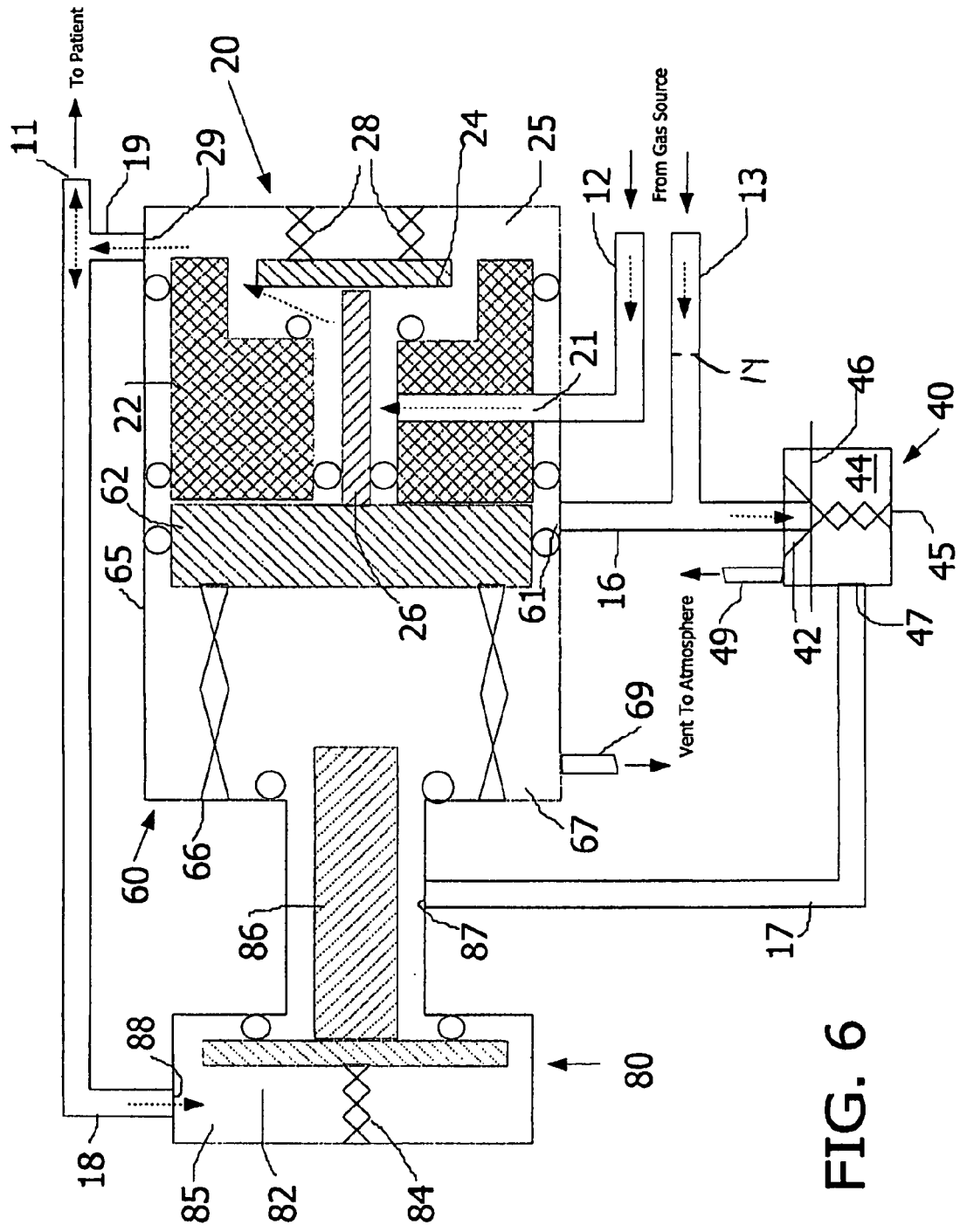
FIG. 6 is a schematic diagram of the conserving device of FIG. 2 illustrating the control piston at the top of its stroke.

FIG. 6 is a schematic diagram illustrating the control piston 62 at the top of its stroke. Before reaching the top of the stroke, however, the control piston 62 engages the delivery actuating rod 26, which overcomes the force of the delivery springs 28 to unseal the delivery plate 24. As soon as the delivery plate 24 is unsealed, the delivery valve 20 is open and low-pressure supply oxygen begins flowing from the delivery inlet 21 through the delivery outlet 29 and on to the patient. The oxygen flow continues until the delivery valve 20 is closed.

Note that to reach the patient, the oxygen enters the flow passageway 19. Because the detection passageway 18 is connected with the flow passageway 19, delivery oxygen also flows into the detection passageway 18 and the check valve cavity 85. Before the delivery valve 20 is opened, however, the check valve 80 has been closed, as described above. Because the check valve 80 is closed, the sensing chamber 44 is isolated from the check valve cavity 85 and, thus, the delivery oxygen flow. The gas flow into the detection passageway 18 will pressurize the check valve cavity 85 and apply further force to seal the check valve plate 82, but will not harm the check valve 80.

At the top of the control piston's stroke, the control gas chamber 68 is essentially empty or at least depressurized enough so that the bias spring 45 can seal the nozzle 42 with the sensing valve membrane 46. Once the nozzle is sealed, gas from the control passageway 16 can no longer escape to atmosphere, causing pressure to build. The control gas chamber 68 will now begin pressurizing via timing gas passing through the control passageway 16.

Figure 7:
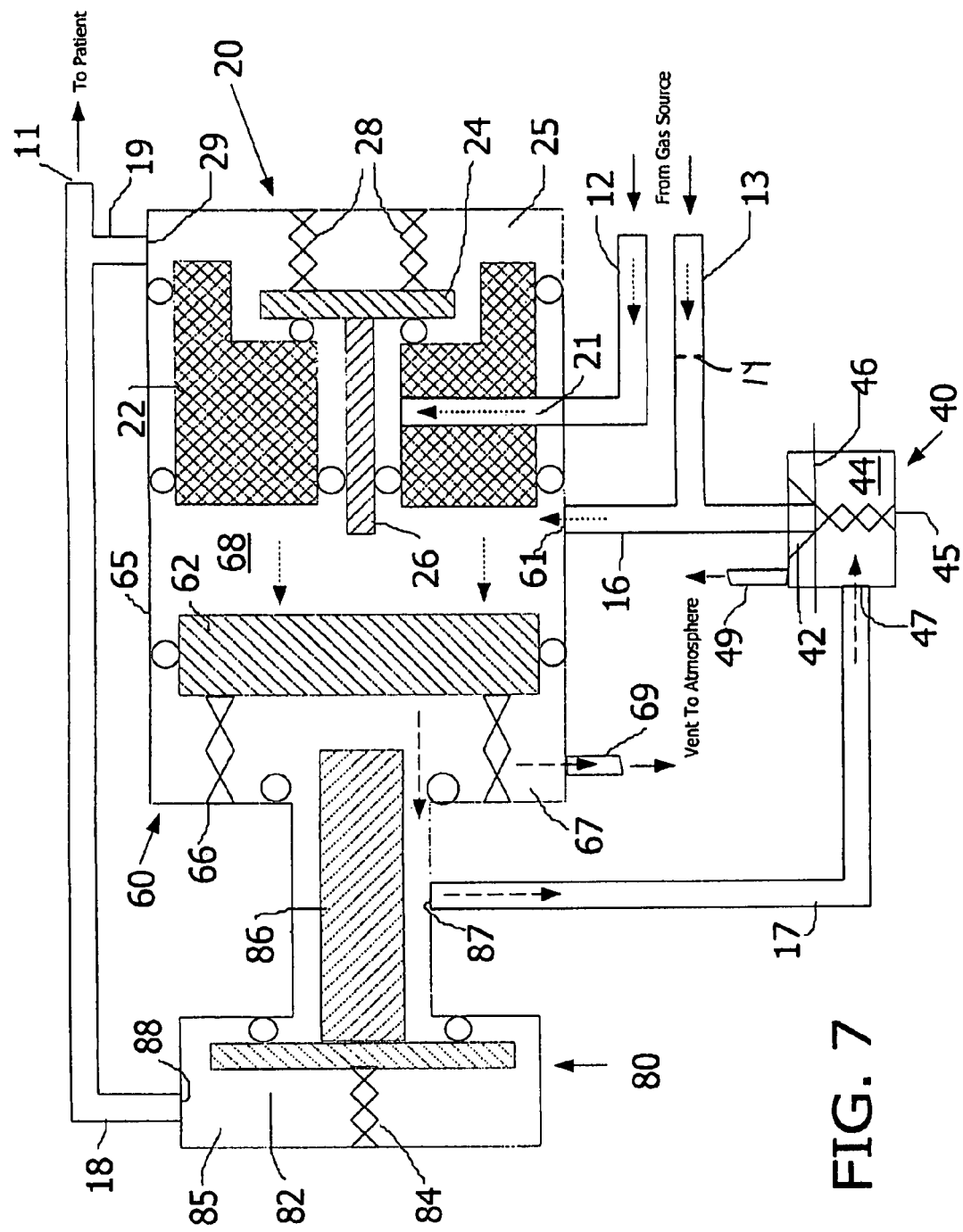
FIG. 7 is a schematic diagram of the conserving device of FIG. 2 illustrating the control piston during its down stroke.

FIG. 7 is a schematic diagram illustrating the control piston 62 during its down stroke. As shown, the control gas chamber 68 is being pressurized. As pressure builds toward the supply pressure, the force of the control springs 66 is overcome, allowing the control piston 62 to compress the control springs 66. At a fixed point during the down stroke, the control piston 62 disengages from the delivery actuating rod 26, thus allowing the delivery springs 28 to compress the delivery plate 24 against the face seals to close the delivery valve. At the point shown, oxygen is not flowing to the patient and the conserver 10 is not ready to detect an inhalation because the check valve 80 is still closed.

The length of the delivery actuating rod 26 is chosen to maintain contact with the control piston 26 for a fixed period of time, such as 400 milliseconds. That provides the patient with a pulse of oxygen for that fixed period of time. Because there is no reservoir to provide an initial burst of oxygen, the conserver provides a fixed flow rate during delivery. Furthermore, the timing orifice 14 is used to reduce the flow rate of timing gas into the control gas chamber 68 and thus inhibit the chance of the device resetting too quickly and delivering a double pulse of gas.

Once the control gas chamber is pressurized, the control piston 62 will engage the check valve actuating rod 86. The actuating rod 86 will lift the check valve plate 82 away from the O-ring and re-couple the patient to the sensing chamber 44, as shown in FIG. 2. At that stage, the conserver 10 is ready to begin a new delivery cycle.

One feature of the conserver 10 is its ability to detect an inhalation and, in response, rapidly deliver oxygen to the patient. This is accomplished by maintaining a small control gas cavity so that the control piston 62 has a short stroke. In addition, a low-friction liner can be placed on the wall of the control gas cavity 68 so that the control piston's O-ring encounters less friction, thus allowing faster piston strokes and providing longer life to the O-ring. Suitable low-friction materials include TEFLON-impregnated nickel, and plastics. The cavities for the delivery valve 20 and the check valve 80 should also be small.

While the conserver 10 should respond rapidly to an inhalation, it is also important that the conserver does not reset too quickly. The time needed for the control piston 62 to complete its down stroke and engage the check valve actuating rod 86 is timed to reduce the likelihood of a double pulse. That timing is determined by the flow rate of oxygen into the control chamber 68, which can be set by selecting the diameter of the timing orifice 14 in the timing passageway 13. During manufacture, the conserver 10 can be set for a one of a plurality of breathing patterns. More generally, an adjustable restrictor could be employed, such as an orifice plate in the regulator 5 (FIG. 1).

In a particular embodiment, the control piston 62 has a stroke period to accommodate patients with a breathing rate in a range of about 16-50 breaths per minute. More particularly, the control piston 62 has a stoke period of about 1.2 seconds, essentially all of which is consumed by the down stroke as the control chamber 68 pressurizes. The delivery actuating rod 26 is dimensioned so that the delivery valve 20 is open for a duty cycle of about 400 milliseconds during the down stroke of the control piston 62. Different timings can be used, however, such as a stroke period of about 1.0 seconds and a delivery duty cycle of between 400-600 milliseconds. Because the timing depends on the volume of the control chamber 62, the use of an adjustable control chamber, employing the techniques described in the above-incorporated U.S. application Ser. No. 10/706,872, can allow the timing to be adjusted in the field.

It is also noted that the control valve vent 69 has an effect on the length of the pulse of gas to the patient as well as the timing after the pulse before the conserver is reset to its steady-state condition (FIG. 2). In a particular embodiment, an adjustable needle valve is disposed within the vent 69, which allows the vent orifice 69 to be controlled during assembly so as to tune the conserver to a specific flow profile. In a particular embodiment, the conserver has an adjustable delivery cycle of between 400 milliseconds and 1200 milliseconds, including a 200 millisecond delay from inhalation until the gas delivery begins.

In addition, the regulator can provide a variable flow rate of oxygen based on a flow rate selected by a user. In this way, the conserver 10 can deliver a variable rate of oxygen for fixed periods of time. The variable flow rate can be provided by the orifice plate in the regulator 5 (FIG. 1).

It should also be understood that the conserver can include a continuous-flow mode, in addition to the conserving mode described above. In particular, the conserver can include a user-selectable conserving or continuous knob or switch, which can be coupled to a valve that allows supply gas flow through the timing passageway 13 when in conserving mode and blocks supply gas flow through the timing passageway 13 when in continuous mode. In such an embodiment, the regulator orifice plate could employ two sets of flow orifices to provide the appropriate gas flows at both settings. When in conserving mode, a selected pair of orifices would provide oxygen to the delivery passageway 12, while in conserving mode, only one orifice of the pair would provide oxygen to the delivery passageway 12, as controlled by the valve. Note that even in the continuous flow mode, the constant flow rate can be selected by the user from a plurality of flow rates, as provided by the orifice plate. A suitable orifice plate for the regulator 5 is described in the above-incorporated U.S. application Ser. No. 10/706,872.

In another embodiment, the delivery valve 20 is shunted when the conserver is in continuous mode. This embodiment offers certain advantages. One advantage is that possible leaking of timing gas into the control gas chamber 68 would not stop continuous flow because the delivery valve 20 is bypassed. Another advantage is that an initial inhalation is not needed to initiate the continuous flow.

Although the invention has been described as not requiring a bolus reservoir, one of ordinary skill in the art can add a reservoir. In one embodiment, a reservoir can be formed between the delivery inlet 21 and the delivery valve plate 24 that could be filled between delivery cycles. Another approach is to use the control gas chamber 68 as a reservoir by replacing the sensing valve vent 49 with a passageway to the delivery inlet 21 and adjusting the bias of the sensing membrane accordingly. A reservoir can also be added by reorienting the valves.

Although a particular valve type is shown for the delivery valve 20 and the check valve 80, other suitable valves can be substituted. For example, the orientation of the passageways can be reversed with respect to the illustrated valves. In the delivery valve, in particular, the delivery passageway 12 could terminate at an inlet in the delivery valve cavity 25 and the delivery outlet could be through the delivery valve body 22 on the opposite side of the delivery plate 24. That arrangement would permit the delivery valve cavity 25 to become pressurized and used as a bolus reservoir for supplying an initial burst of oxygen to the patient. A similar valve structure could be used for the check valve 80. Other valve types can be used and are a design choice.

Figure 8:
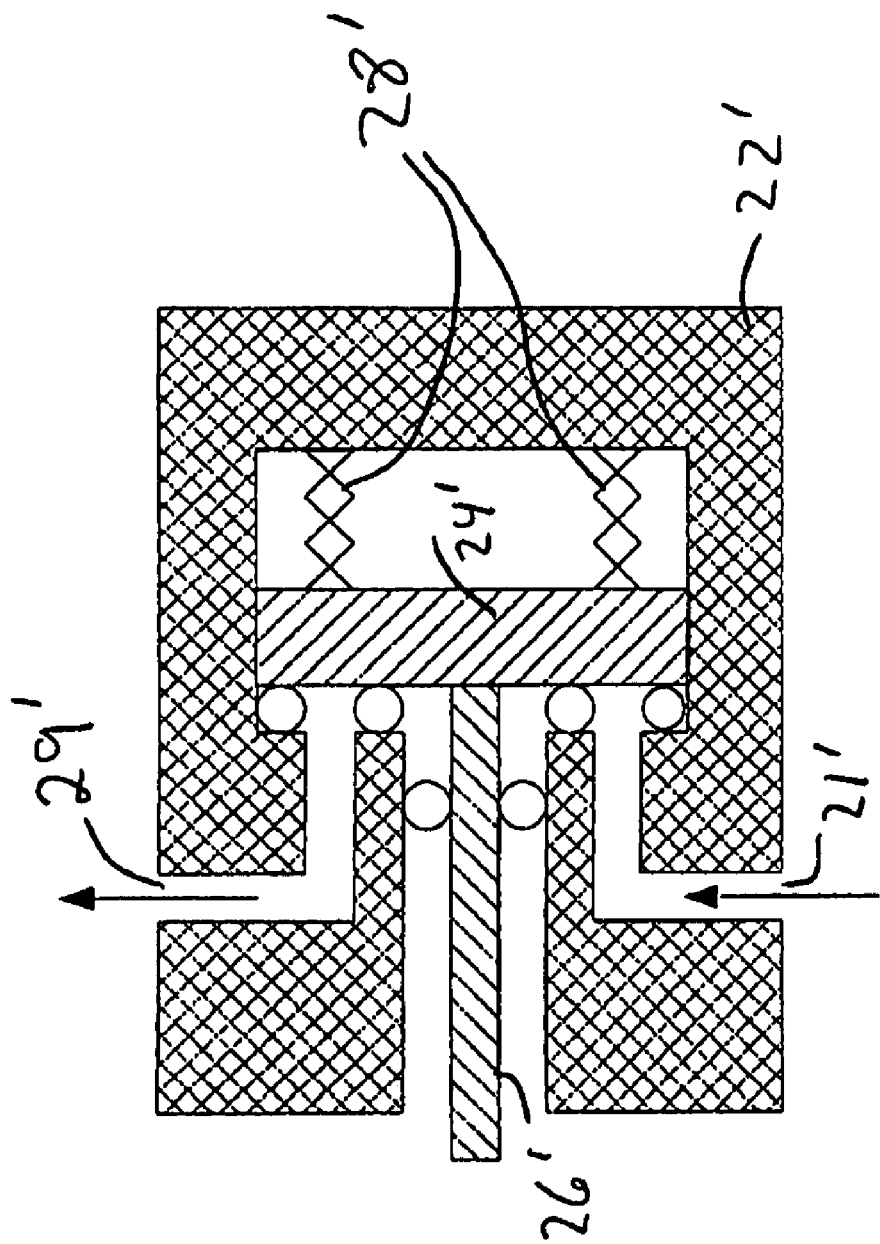
FIG. 8 is an example of another suitable delivery valve that can be used in the conserving device of FIGS. 2-7.

FIG. 8 is an example of another suitable delivery valve 20' that can be used in the conserving device of FIGS. 2-7. As illustrated, delivery valve body 22' includes an inlet 21' and an outlet 29' that are sealed against a common face of a valve plate 24' by O-rings when the valve is closed and unsealed from the O-rings when the valve is open. Note that in this particular structure, the O-rings are redundant. Also shown are a delivery actuating rod 26' and delivery valve springs 28'.

The conserver components are made from typical materials known in the art to be oxygen compatible, including aluminum, brass, titanium, and nickel. The particular materials used for each component part is an engineering choice. In one particular embodiment, the delivery valve body 22 and the moveable components are fabricated from brass.

Although the delivery of oxygen is most common use of a medical gas conserver, the delivery of other therapeutic gases is contemplated, for example, nitrous oxide. In addition, the present invention can be employed for non-therapeutic uses, such as for the delivery of lethal gases, or the delivery of other gases for industrial uses.

While this invention has been particularly shown and described with references to particular embodiments, it will be understood by those skilled in the art that various changes in form and details may be made without departing from the scope of the invention encompassed by the appended claims. For example, various features of the embodiments described and shown can be omitted or combined with each other.

What is claimed is:

1. A pneumatic medical gas conserver for providing a volume of medical gas to a patient, comprising: a supply port for receiving a regulated flow of a medical gas; a patient port for providing a flow of medical gas to a patient through a single-lumen cannula; a sensing valve in gaseous communication with the patient port for detecting an inhalation by the patient to trigger delivery of the medical gas to the patient port; and a check valve gaseously disposed between the sensing valve and the patient port for decoupling the sensing valve from the patient port in response to detection of the inhalation by the sensing valve.

2. The conserver of claim 1 wherein the check valve decouples the sensing valve from the patient port before the medical gas is delivered to the patient port.

3. The conserver of claim 1 wherein the decoupled sensing valve is gaseously isolated from the delivered medical gas.

4. The conserver of claim 1 further comprising a gas regulator in gas communication with the supply port.

5. A pneumatic medical gas conserver for providing a volume of medical gas to a patient, comprising: a patient port for coupling to a single-lumen cannula; a supply port for receiving a regulated flow of a medical gas; a delivery valve gaseously disposed between the supply port and the patient port for controlling the flow of medical gas to the patient port; a control valve in mechanical communication with the delivery valve and in gas communication with the supply port for actuating the delivery valve; a sensing valve in gas communication with the control valve and the patient port for detecting an inhalation by the patient to trigger the control valve to begin a delivery cycle; and a check valve in mechanical communication with the control valve and gaseously disposed between the sensing valve and the patient port for decoupling the sensing valve from the patient port in response to detection of the inhalation by the sensing valve.

6. The conserver of claim 5 further comprising a gas regulator for providing the regulated flow of medical gas from a pressurized supply of the medical gas, the gas regulator in gas communication with the supply port.

7. The conserver of claim 6 wherein the gas regulator provides a user selectable flow of medical gas from a plurality of flow settings.

8. The conserver of claim 5 further comprising a user-operable flow valve for selecting between a pulse delivery mode and a constant flow mode.

9. The conserver of claim 8 wherein the constant flow mode causes the flow of medical gas to bypass the delivery valve.

10. The conserver of claim 5 wherein the control valve is tuned to provide a fixed delivery cycle.

11. The conserver of claim 10 wherein the control valve includes an adjustable needle to vent gas.

12. The conserver of claim 10 further comprising a timing orifice disposed in the gas flow path from the supply port to the control valve.

13. The conserver of claim 5 wherein the sensing valve includes a flexible membrane.

14. A pneumatic medical gas conserver for providing a volume of medical gas to a patient, comprising: a housing connectable to a supply of pressurized medical gas; a gas flow regulator within the housing for providing a regulated flow of medical gas from the supply of pressurized medical gas, the regulated flow including a user-selectable flow rate from a plurality of selectable flow rates; a patient port within the housing for providing gas communication to a patient through a single-lumen cannula; a user-operable mode selector within the housing for providing the regulated flow of medical gas to the patient port at the selected flow rate in either a pulse flow mode or a constant flow mode; and a pneumatic delivery circuit within the housing for receiving the regulated flow of medical gas and delivering the received flow to the patient port in accordance with the mode selector; and within said pneumatic delivery circuit, a check valve in mechanical communication with a control valve and gaseously disposed between a sensing valve and said patient port for decoupling the sensing valve from said patient port in response to detection of patient inhalation by the sensing valve.

15. The conserver of claim 14 wherein the delivery circuit includes a delivery valve.

16. The conserver of claim 15 wherein the regulated flow of medical gas bypasses the delivery valve when the mode selector is in the constant flow mode setting.

17. The conserver of claim 15 wherein the regulated flow of medical gas travels through the delivery valve when the mode selector is in the constant flow mode setting.

* * * * *